(12) United States Patent
Yeo (10) Patent No.: US 7,432,510 B2
(45) Date of Patent: Oct. 7, 2008

(54) DOSIMETER BASED ON A GAS ELECTRON MULTIPLIER FOR DOSE MEASUREMENTS OF THERAPEUTIC RADIATION

(76) Inventor: In Hwan Yeo, 5 Audrey Ct., Voorhees, NJ (US) 08043

( * ) Notice: Subject to any disclaimer, the term of this patent is extended or adjusted under 35 U.S.C. 154(b) by 74 days.

(21) Appl. No.: 11/497,076

(22) Filed: Aug. 1, 2006

(65) Prior Publication Data
US 2008/0029709 A1 Feb. 7, 2008

Related U.S. Application Data

(60) Provisional application No. 60/716,758, filed on Sep. 13, 2005.

(51) Int. Cl.
*H01J 47/00* (2006.01)
(52) U.S. Cl. ............................................. 250/374
(58) Field of Classification Search ............... 250/374
See application file for complete search history.

(56) References Cited

U.S. PATENT DOCUMENTS

| | | | |
|---|---|---|---|
| 3,022,424 A | 2/1962 | Anton | |
| 3,274,328 A | 9/1966 | Davis | |
| 6,316,773 B1 | 11/2001 | Giakos | |
| 7,030,386 B2 * | 4/2006 | Pang et al. | 250/370.14 |
| 2002/0149305 A1 | 10/2002 | Danielsson et al. | |

FOREIGN PATENT DOCUMENTS

| | | |
|---|---|---|
| WO | WO 99/21211 | 4/1999 |
| WO | PCT/US2006/032437 | 8/2006 |

OTHER PUBLICATIONS

U.S. Appl. No. 60/716,758, filed Sep. 13, 2005, In Hwan Yeo.
Brown et al.; MCNP—A General Monte Carlo N-Particle Transport Code, Version 5 vol. II: User's Guide; Los Alamos National Laboratory, dist. by the RSICC of ORNL (2003).

* cited by examiner

*Primary Examiner*—Constantine Hannaher
*Assistant Examiner*—Marcus H Taningco
(74) *Attorney, Agent, or Firm*—Williamson Intellectual Property Law, LLC; Thomas R. Williamson, III (57) ABSTRACT

A dosimeter based on a gas electron multiplier and method of use thereof for measurement of doses of therapeutic radiation to which a tissue-phantom is exposed. Subsequent to the in-phantom measurement and verification of radiation beam delivery, radiation can be effectively delivered to a human target organ, based on the verification of radiation quantities to which the phantom was exposed. Use of a gas electron multiplier-based dosimeter facilitates precise and accurate verification of the radiation dose within a phantom by taking measurements in real time, with no need for subsequent film processing.

27 Claims, 4 Drawing Sheets

Tissue-equivalent GEM-based detector and application

FIG 1A. Tissue-equivalent GEM-based detector and application

FIG 1B. Diagram of GEM

FIG 1C. Diagram of Aperture/Grid Structure

DOSIMETER BASED ON A GAS ELECTRON MULTIPLIER FOR DOSE MEASUREMENTS OF THERAPEUTIC RADIATION

PRIORITY CLAIM

To the fullest extent permitted by law, this non-provisional patent application claims priority to, and the full benefit of, U.S. Provisional Patent Application No. 60/716,758, filed Sep. 13, 2005, entitled "Dosimeter Based on a Gas Electron Multiplier for Dose Measurements of Therapeutic Radiation".

TECHNICAL FIELD

The present invention relates generally to radiation detectors, and more specifically to a dosimeter based on a gas electron multiplier for measurement and verification of radiation doses utilized in, but not limited to, radiation therapy.

BACKGROUND OF THE INVENTION

Dosimetric verification of radiation therapy is a very important procedure, as successful radiation therapy requires an accurate delivery of dose to a cancerous volume of tissue. Accordingly, when treating patients with radiation, it is desirable to quantify the dose of radiation that will be applied and to verify that such quantified dose will be delivered by the equipment to be utilized. Further, it is believed that a decrease of 10 to 15% in dose delivery will result in a decrease in the chance of cure by a factor of two or three times, while an increase in dose will similarly increase the chance of irreversible damage. Therefore, accurate and specific dose levels are critical to the success rate of patient treatment.

One such method of treating patients is with x-radiation Intensity Modulated Radiation Therapy (IMRT). With IMRT, the radiation is delivered as many tiny, pencil-thin radiation beams (i.e. beamlets), with characterized weights in radiation dose for each beamlet, wherein the beams enter the body from many angles to destroy cancer cells. This accurate delivery of beamlets permits a higher dose of radiation to be delivered to tumors and limits the dose to surrounding healthy tissue, thereby reducing radiation side effects. In this fashion, IMRT can be utilized to safely treat tumors including, for exemplary purposes only, those located near critical organs, such as the eyes and the spinal cord.

To implement treatment, IMRT is computationally planned, based on the computed tomography image of a patient. Computed tomography, or CT, is an x-ray diagnostic procedure utilized to generate a three-dimensional image of a patient, wherein the resulting image is composed of a multitude of cross-sectional views. CT requires data acquisition, image reconstruction and image display. To collect data, x-rays are passed through a patient and are attenuated within the patient, wherein the resulting levels of x-rays are sensed by external detectors to allow the creation of a detailed image of the internal composition of the patient. By moving the x-ray source and taking multiple images, detailed cross-sections can be produced, which then can be utilized to form a three-dimensional image of the patient for accurate selection of the target area to be treated. Once the CT image has been formed and the target area position elucidated and selected, IMRT optimization (in weights and positions of beamlets) is performed to achieve the desired dose distribution in the target and surrounding organs.

Prior to performing IMRT, verification of the radiation levels for the therapy is performed. Typically, a "phantom", or tissue mimic, is utilized to assist in such verification. First, beams that were optimized for patient treatment are delivered upon a flat phantom, and the consequent dose distributions at some specific depth are calculated for each beam. Second, beams are actually delivered on a phantom that houses a planar dosimeter under a medical linear accelerator, thereby generating signals on the dosimeter. The planar signals are converted into a dose distribution, which is then compared with the dose distribution obtained by calculation. If the difference between the calculations and the actual measurements are within acceptable parameters, the treatment based on the computationally-optimized beam commences on a patient.

As stated above, IMRT requires pretreatment verification based on dose measurement, taken by applying radiation to a phantom that simulates the human organ/tissue. IMRT delivers a radiation dose conforming to the volume of a target only, thus saving exposure of normal and/or critical organs to radiation. In so doing, IMRT generates a non-uniform dose distribution that potentially has a rapid dose gradient. This feature of IMRT puts more demand on multi-dimensional dosimeters, requiring fine spatial resolution and dose integration, in addition to the traditional properties of tissue (or water)-equivalent dose response and real-time data acquisition.

Existing methods of dosimetry include the use of instruments such as ionization chambers (IC), thermoluminescent dosimeters (TLD), and diode detectors. An IC is universally regarded as the standard dosimeter for calibration and dose measurement for radiation therapy, and an IC/water phantom system has been recommended for isodose distribution measurement. However, IC/water phantom systems have some shortcomings in operation. Measurement with an IC provides only selective information with poor resolution. That is, each point-wise datum is limited by its volume and the spacing between measurements. In addition, measurement time using IC/water phantom systems is relatively long. Furthermore, dynamic beam-defining multileaf-collimators and wedges have complicated measurement of doses, taken utilizing IC/water phantom systems.

For dynamic beam dosimetry, a large array IC/water phantom system must be utilized to simultaneously measure doses at various positions in a phantom. However, in addition to the economic disadvantage, simultaneously placing a large number of ICs in a phantom alters the dose distribution being measured and limits spatial resolution (currently-used dosimeters typically have spacing of 7 mm). Such inadequacy similarly applies to TLDs and diode detectors. Therefore, improved dosimeters are needed.

In an effort to overcome the aforementioned deficiencies, and develop a multidimensional dosimeter, prior designs have included use of a TLD plate, plastic scintillators, radiographic (x-ray) film, tissue-equivalent gel, and electronic portal imaging devices (EPID). For instance, a TLD plate utilizing tissue-equivalent elements has been tried. Unfortunately, the diameter of the laser beam reader (i.e., 1.7 mm) limited the spatial resolution of the TLD plate, wherein for isodose measurement of a cobalt-60 radiotherapy beam in a water phantom, the plate showed a relatively high deviation of 14% from measurements utilizing ICs. Such a deviation suggests that utilizing a TLD plate dosimeter requires technically-challenging fabrication of a relatively large plate-type TLD with uniform thickness, in addition to stabilizing material properties, particularly against embrittlement and laser heating.

The potential of utilizing a plastic scintillator for two-dimensional dose measurement of megavoltage beams was first realized through incorporating a digital camera as a light receptor. Other attempts have utilized a plastic scintillator combined with an optical fiber and a photomultiplier tube for brachytherapy dose measurement. Material properties of the scintillator have even been modified to suit dose measurement of low-energy brachytherapy sources. However, no effort utilizing scintillators has been directed to photon beam measurement of IMRT.

Thin radiochromic film has been investigated and utilized as a dosimeter for brachytherapy and less frequently for external radiotherapy that includes stereotactic radiotherapy and IMRT. Such film has relatively good tissue equivalence. In addition to the excellent features inherent in thin film dosimeters, no post-irradiation processing is required for radiochromic film. However, radiochromic film has several undesirable features as a dosimeter: (1) radiochromic film is much more expensive than radiographic film, (2) the optical density of the film after exposure changes with time, which requires an additional calibration of optical density to time, (3) inherent error of uncertainty per single sheet of the film is relatively large (e.g., 1-5% after noise reduction) compared with that of radiographic film (e.g., 0.5% without any processing), and (4) due to the low sensitivity of radiochromic film, a relatively large dose (a few grays (Gy)) is required for a longer exposure time than is required with radiographic film (a few cGy).

Radiographic (x-ray) film has been utilized extensively for IMRT. This is because radiographic film (1) has excellent spatial resolution limited mainly by the grain size in the film emulsion (less than 1 micron) and the aperture of the light beam in a densitometer, (2) has a uniform sensor thickness and response across the film (<0.5% difference on films processed simultaneously), (3) requires relatively short measurement time (less than a few hours including experiment and dose acquisition), (4) is currently inexpensive (e.g., a few dollars for a single sheet of KODAK X-OMAT film—KODAK and X-OMAT are registered trademarks of Eastman Kodak Company), (5) integrates the dose and is thus suited for dynamic beam measurement, and (6) involves a relatively simple measurement setup and procedure, involving a plastic water phantom rather than a liquid water phantom. However, radiographic film suffers from energy-dependent response (and thus inaccuracy) as well as requiring post-irradiation processing (i.e., real-time data acquisition is difficult).

Gel dosimetry using magnetic resonance (MR) imaging technique or optical computed tomography has been studied for three-dimensional work. This technique can provide accurate dose measurements since it employs a practical tissue-equivalent medium that can be molded into a desired shape for use as a dosimeter. However, gel dosimetry is associated with some or all of the following technical difficulties: unavailability of a dedicated MR unit, relatively high expense associated with its operation, difficulties in gel handling, non-uniformity of a magnetic field, variability in the gel manufacturing process, and so on.

Electronic portal imaging devices (EPID) have been investigated for dose verification. Dosimetry utilizing an EPID is normally compared to calculations, using a treatment planning system for verification. However, calculations from a model-based planning system cannot accurately reproduce the exit dose measured in an aSi-based EPID with a scintillation screen containing a Gd-compound. This is due to the over-response of the compound to low-energy photons, unlike the liquid ion chamber-based EPID. In addition, modeling back-scattered photons entering into the aSi-based EPID is not an easy task; although, exit doses have previously been modeled on an aSi-based EPID accurately utilizing a Monte Carlo technique when compared to a measured dose. Furthermore, the calculation suffered from long calculation time (e.g., it took one hour for one IMRT field; thus, for multiple IMRT fields it would require several hours). Modeling all the necessary structural components and back-scattering would be extremely complex, time consuming and difficult. Therefore, exit dosimetry using the aSi-based EPID is still in the developmental stage. Additionally, EPID is in essence an exit dosimeter rather than an in-phantom dosimeter, whereas an in-phantom dosimeter more actually simulates measurement in a patient.

None of the above dosimeters meet the demand necessitated by IMRT. Therefore, it is readily apparent that there is a need for an improved dosimeter in radiation therapy. As will be more fully detailed hereinbelow, it is to the provision of such an apparatus and method that the present invention is directed.

BRIEF SUMMARY OF THE INVENTION

Radiation therapy requires measurement of the dose of therapeutic radiation beams for either quality assurance or for characterization of the beams. Such measurement includes determining beam profiles that may be uniform or modulated within a field. The measurements are typically taken utilizing a dosimeter having a build-up layer above the dosimeter or a dosimeter that is sandwiched within a phantom stack. An ideal dosimeter should be capable of acquiring integrated tissue-equivalent signals at multiple points with a fine spatial resolution on a two-dimensional plane, wherein the signal is acquired in real time.

Briefly described, in a preferred embodiment, the present invention overcomes the previously-mentioned disadvantages and meets the recognized need for such a device by providing a dosimeter based on a gas electron multiplier.

According to its major aspects and broadly stated, the present invention in its preferred form is a dosimeter based on a gas electron multiplier (or any tissue-equivalent layer perforated with gas holes and coated with conductive layers on both sides) that can be disposed within layers of tissue-equivalent phantom material. When placed in a phantom, the dosimeter based on a gas electron multiplier will detect signals registered by upstream electrons, generated as a result of photon interaction within the phantom, that deposit energy and liberate additional electrons in the gas layer above the gas electron multiplier within the dosimeter. Therefore, the energy and intensity of the photon beam can be measured, and thus verified prior to application to a patient.

More specifically, the dosimeter comprises a cavity, a cavity gas, a gas electron multiplier, a readout board, electrode plates, a detector wall, and optionally a perforated insulating layer. A gas electron multiplier is a tissue-equivalent insulating layer with conductive layers coated on both sides, wherein cavity holes are distributed across the three layers for the retention of gas, and wherein the applied voltage between the conductive layers accelerates and directs electron flow through the holes in proportional counting mode. Gas multiplication thus occurs through the holes. The electron flow is augmented by the electric potential exerted by the electrode plate (cathode) disposed on top of the tissue-equivalent gas layer above the gas electron multiplier. The electrons that are generated by the upstream electrons absorbed in the gas layer are pushed downward into the holes in the gas electron multiplier. The hole, or aperture, diameter and the spacing among neighboring holes can be made smaller than 1 mm, which therefore allows excellent spatial resolutions for two-dimensional in-phantom dose measurement. The dosimeter can also be utilized to readout any entering radiation without any or little build-up (build-up and back-up altogether) phantom.

The gas layer disposed above the gas electron multiplier detector comprises a thickness less than 1 mm. Spatial resolution of the gas layer is adapted to be less than 2 mm in a horizontal dimension perpendicular to a beam entry direction. The optional perforated layer comprises a thickness of approximately 2 to approximately 4 millimeters and a plurality of apertures having a diameter of approximately 3 millimeters. This perforated layer replaces the gas layer above the gas electron multiplier.

The perforated layer comprises an aperture/grid structure, wherein said aperture/grid structure comprised of a tissue-equivalent, non-conductive, radiation-resistant plastic material and is adapted to prevent crosstalk. The aperture/grid structure comprises polystyrene cross-linked with divinylbenzene.

The dosimeter based on a gas electron multiplier is operated in either pulse or current mode, and can be operated in either gas-flow or gas-sealed environments. The dosimeter based on a gas electron multiplier is utilized for reading therapeutic radiation dose, wherein tissue-equivalent signals are generated utilizing a tissue-equivalent dosimeter wall, tissue-equivalent conductive and insulating layers, and a tissue-equivalent gas which absorbs ionizing radiation.

Accordingly, a feature and advantage of the present invention is its ability to utilize thin plate-like geometry to facilitate sandwiching of the dosimeter based on gas electron multiplier (or any tissue-equivalent perforated layer, coated with conductive layers, with cavity holes containing gas) between two phantom slabs for in-phantom dosimetry measurement, or radiation readout such, as multileaf collimator positioning with no or little in-phantom buildup.

Another feature and advantage of the present invention is its ability to respond to various ionizing radiation (γ-ray, X-ray, electrons, charged particles, and neutrons), and is not limited to therapeutic purposes.

Still another feature and advantage of the present invention is that it requires little or no correction to obtain a true dose applied to a phantom.

Yet another feature and advantage of the present invention is its straightforward technology for fabricating a single detector that contains a large number of small gas cavities.

Yet another feature and advantage of the present invention is its ability to operate in gas-sealed environment, as well as gas-flow environment.

Yet still another feature and advantage of the present invention is that data is acquired in real-time.

A further feature and advantage of the present invention is its ability to operate in either current mode or pulse mode.

Still a further feature and advantage of the present invention is its ability to detect uniform beams, as well as intensity-modulated beams.

These and other features and advantages of the present invention will become more apparent to one skilled in the art from the following description and claims when read in light of the accompanying drawings.

BRIEF DESCRIPTION OF THE DRAWINGS

The present invention will be better understood by reading the Detailed Description of the Preferred and Selected Alternate Embodiments with reference to the accompanying drawing figures, in which like reference numerals denote similar structure and refer to like elements throughout, and in which.

DETAILED DESCRIPTION OF THE PREFERRED AND SELECTED ALTERNATIVE EMBODIMENTS

In describing the preferred and selected alternate embodiments of the present invention, as illustrated in FIGS. 1A-3, specific terminology is employed for the sake of clarity. The invention, however, is not intended to be limited to the specific terminology so selected, and it is to be understood that each specific element includes all technical equivalents that operate in a similar manner to accomplish similar functions.

Figure 1A:
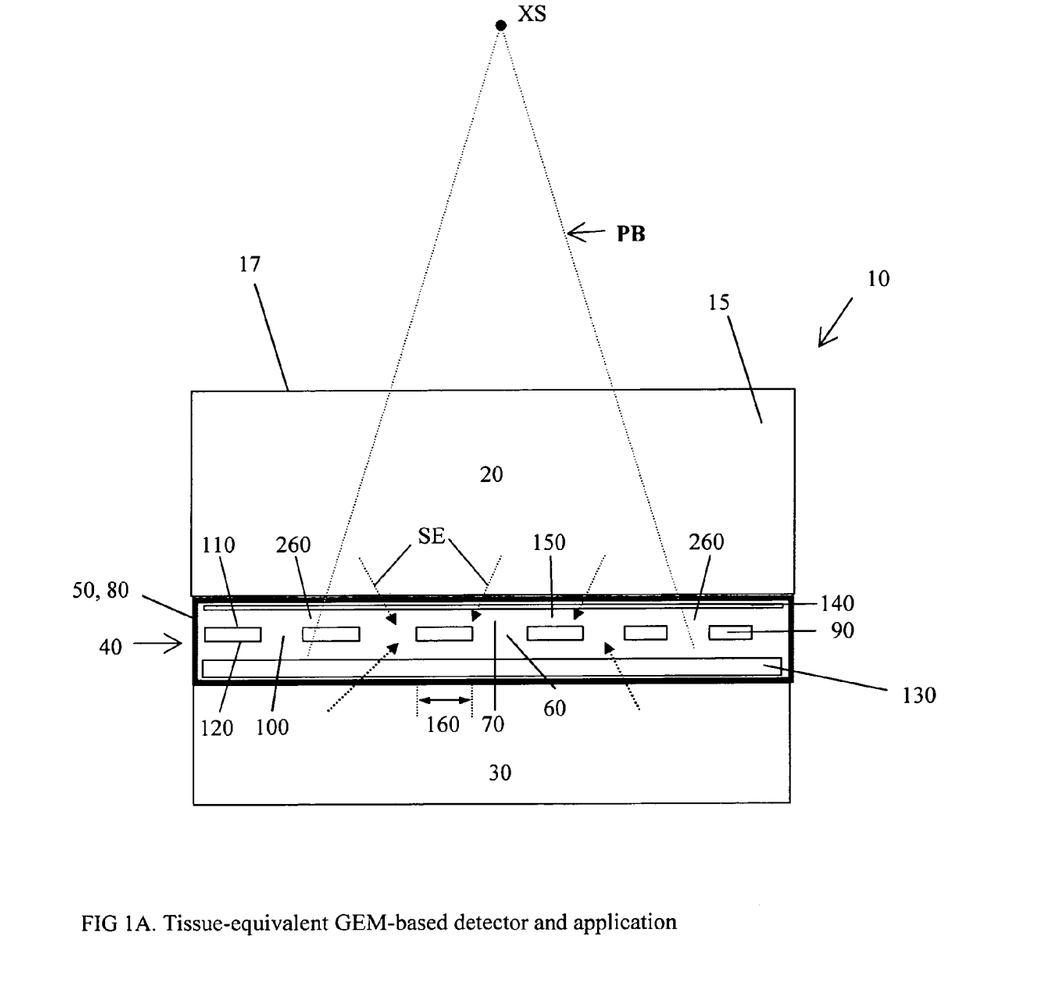
FIG. 1A is a cross-sectional view of a dosimeter based on gas electron multiplier according to a preferred embodiment of the present invention, shown in an x-ray system including human-tissue phantoms.
Figure 1B:
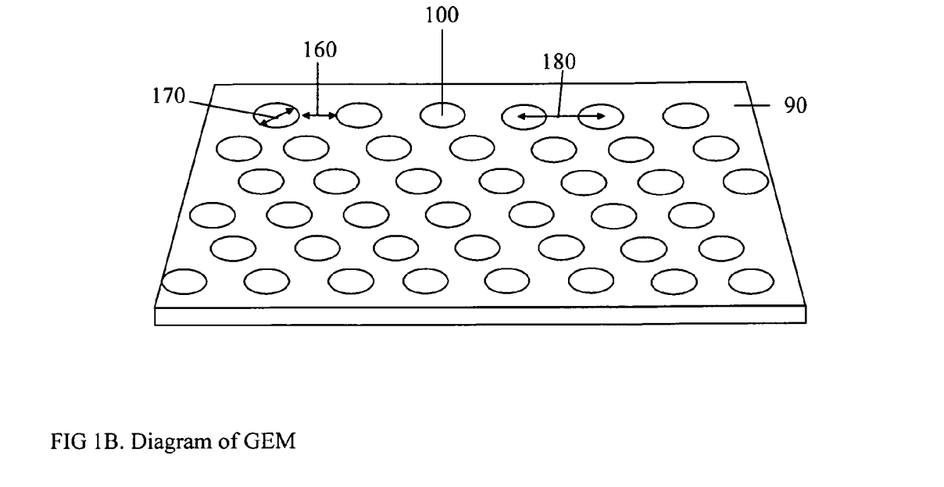
FIG. 1B is a top view of a gas electron multiplier (GEM) layer according to the dosimeter of FIG. 1A.

Referring now to FIGS. 1A-1B, the present invention in a preferred embodiment is a gas electron multiplier-based (GEM) dosimeter 40, wherein GEM-based dosimeter 40 preferably comprises housing 50, tissue-equivalent GEM layer 90, gas cavity 60, tissue-equivalent gas 70, electrode plate 140 and readout board 130. Detector housing 50 preferably comprises detector wall 80. GEM-based dosimeter 40 is preferably disposed between buildup phantom layer 15, wherein buildup phantom layer 15 preferably comprises top build-up phantom layer 20 and bottom back-up phantom layer 30, wherein buildup phantom layer 15 and GEM-based dosimeter 40 are disposed within dosimeter apparatus 10. Phantom layers 20, 30 are preferably comprised of material that is tissue-equivalent. That is, the material of phantom layers 20, 30 preferably absorbs radiation in the same fashion and with the same characteristics as human tissue in terms of absorbed dose. Build-up and backup layers 20, 30 comprise thicknesses selected according to dosimetric needs dependent upon the type of application that the dosimeter is being utilized for.

GEM layer 90 comprises a two-dimensional plastic layer with perforations, such as apertures 100, equally distributed thereacross, wherein the two surfaces are coated with conductive layers 110 and 120. Voltage is applied across GEM layer 90 between first surface 110 and second surface 120. Readout 130 is disposed below GEM layer 90, wherein GEM layer 90 and readout 130 are disposed within housing 50. A series of data points are determined from electrons that reach and register on readout 130.

Detector wall 80 of housing 50 preferably comprises a tissue-equivalent plastic material. Housing 50 is filled with tissue-equivalent gas 70. Tissue (or water) equivalence is characterized in terms of the average atomic number in the elemental composition of materials. For example, nitrogen, whose atomic number (AN=7) is nearly equal to that of a water molecule (AN=8), is a tissue-equivalent gas, since tissue is mostly comprised of water. Plastic solid-water materials and materials such as plastic conductor A-150 (distributed by Standard Imaging, Inc. 7601 Murphy Drive, Middleton, Wis. 53562-2532), are tissue-equivalent. Additional structures such as electrode plates 140 can be disposed as a cathode within housing 50 of GEM-based dosimeter 40 to enhance the functionality of GEM-based dosimeter 40, wherein electrode plates apply a gradient to move and accelerate/decelerate electrons. The electrode plate 140 can be made of tissue-equivalent conductive plastic materials such as A-150. Housing 50, tissue-equivalent gas 70, GEM layer 90, electrode plates 140, and readout board 130 preferably function as a part of tissue phantom 15.

When photon beam PB enters dosimeter apparatus 10, photon beam PB undergoes interactions with tissue-equivalent top and bottom phantom layers 20 and 30, respectively, generating secondary electrons SE. Secondary electrons SE enter tissue-equivalent gaseous area 150 above GEM layer 90 and interact in the gas liberating additional electrons which then pass through apertures 100 of GEM layer 90, wherein the additional electrons register a tissue-equivalent signal directly below apertures 100 onto readout 130. Apertures 100 preferably provide channels for electron flow, with or without electron multiplication (wherein electron flow rises exponentially), and subsequently the electrons provide signal registration. The quantity of electrons registering a signal is proportional to the dose deposited in gas 70 in gaseous area 150, and thus subsequently deposited in tissue of a patient. Pitch 180 among apertures 100 and diameter 170 of apertures 100 preferably define the spatial resolution, which permits measurement of photon beams PB with a high dose gradient and varying degree of beam intensity modulation. Pitch 180 is the distance from the center of one aperture 100 to the center of another aperture 100. Thus, a two-dimensional dose image of photon beam PB can be acquired. Photons from photon beam PB can also enter into gaseous area 150 and generate secondary electrons SE, which can also register as a signal, but to a minimal extent. Charged particles, neutrons and other types of radiation can also enter build-up phantom 20 of various thickness from zero and similarly register tissue-equivalent signals.

Figure 1C:
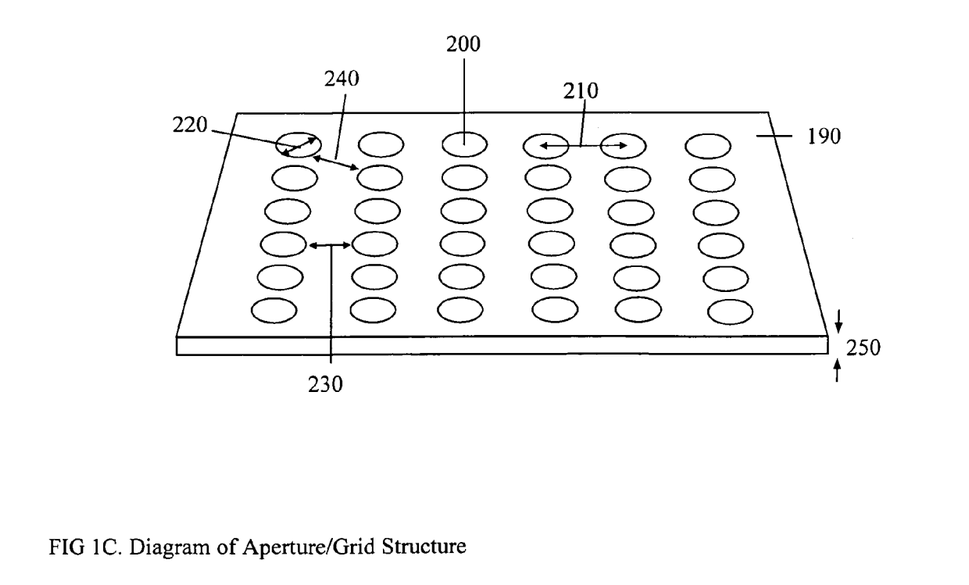
FIG. 1C is a top view of an optional perforated grid screen component disposed above the gas electron multiplier (GEM) layer of FIG. 1B.

Referring now to FIG. 1C, in an alternate configuration, aperture/grid screen 190 can be optionally placed above GEM layer 90 replacing gaseous area 150. Grid screen 190 can be made of tissue-equivalent plastic materials comprising polystyrene cross-linked with divinylbenzene, e.g. REXOLITE, (registered trademark of C-LEC Plastics, Inc.), wherein grid screen 190 comprises circular apertures 200 filled with TP gas. Webs 230, 240 of grid screen 190 prevent lateral cross talk of electrons in apertures 200.

In continuous-current mode, GEM-based dosimeter 40 is equivalent to a large array of ion chambers (ICs). In pulse mode, GEM-based dosimeter 40 is equivalent to a large, array of tissue-equivalent proportional counters which measure both absorbed radiation doses and the corresponding quality of radiation. The pulse mode capability is unique to GEM-based dosimeter 40, and is especially useful in high-LET (Linear Energy Transfer) therapy modalities (e.g., neutron therapy).

Dosimeter 40 can also be operated merely as a reader of radiation position and intensity, including as a multileaf collimator position readout.

EXAMPLE I

Figure 2:
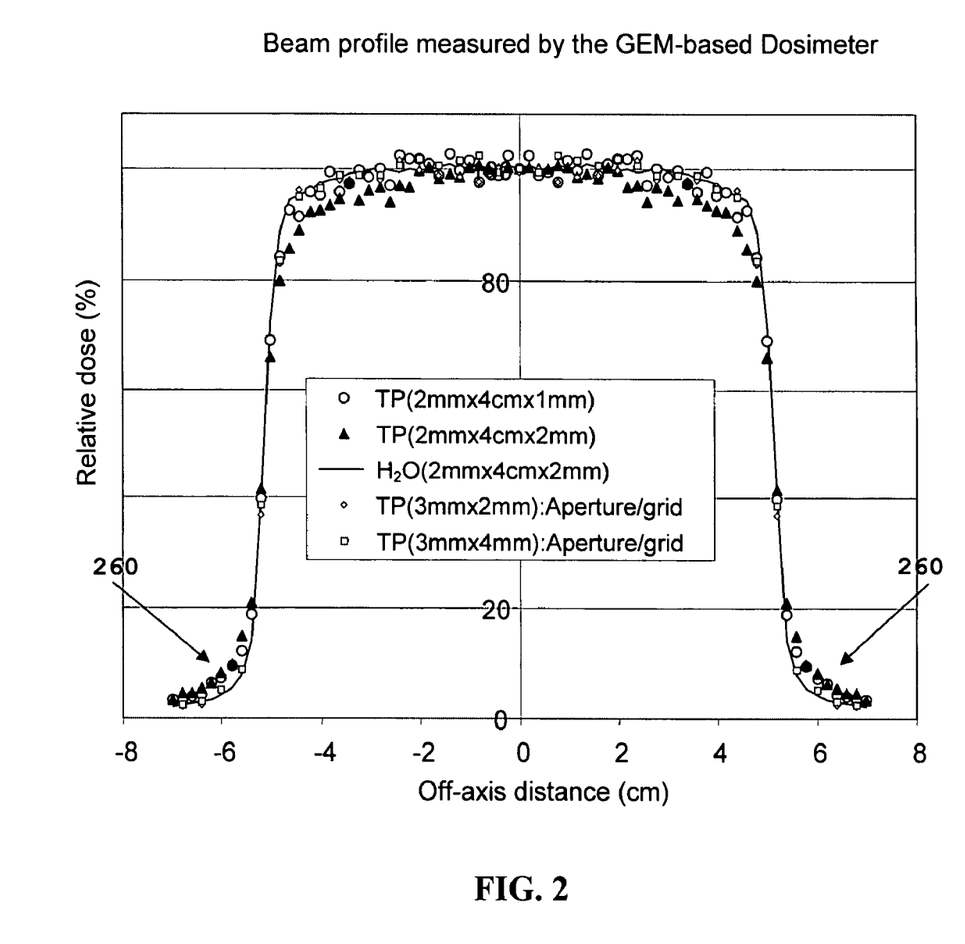
FIG. 2 is a chart depicting relative dose (%) versus off-axis distance (cm) of the GEM-based dosimeter measured at 100 cm from a 6 MV x-ray source being irradiated on the build-up water phantom of 5 cm thickness; and, FIG. 3 is a chart depicting relative dose response versus energy (MeV) of the GEM-based dosimeter measured at 100 cm from a 6 MV x-ray source being irradiated on the build-up water phantom of 5 mm thickness.

Referring now more particularly to FIG. 2, depicted therein is a graph of five dose distributions obtained by computational simulation using a Monte Carlo Particle transport technique (Brown et al.; MCNP—A General Monte Carlo N-Particle Transport Code, Version 5 Volume II: User's Guide; Los Alamos National Laboratory, distributed by the RSICC of the Oak Ridge National Laboratory (2003)). For this simulation, 5 cm thick top build-up phantom layer 20 and bottom backup phantom layers 30 were modeled. Phantom layers 20, 30 comprised water ($H_2O$). Tissue-equivalent GEM layer 90 comprised a thickness of 50 microns, wherein tissue-equivalent GEM layer 90 was coated with copper comprising a thickness of 5 microns on each side of GEM layer 90 on surfaces 110, 120. Tissue-equivalent GEM layer 90 comprised a polyimide film, such as KAPTON (registered trademark of E.I. DuPont de Nemours and Company), having a density of 1.42 g/cc and comprising an elemental composition in weight percent of 2.6 for H, 69 for C, 21 for O, and 7.4 for N. It will be recognized by those skilled in the art that materials other than polyimide films could be utilized without departing from the spirit of the present invention.

Diameter 170 of aperture 100 in GEM layer 90 comprised 50 microns, wherein pitch 180 between adjacent apertures 100 comprised 100 microns and wherein web 160 comprised 50 microns. Tissue-equivalent gas 70 filled gas cavity 60, wherein tissue-equivalent propane (TP) was utilized as gas 70. For TP, the physical density comprised 0.001826 g/cc and the composition in weight percent comprised 10.27 for H, 56.89 for C, 29.34 for O, and 3.5 for N. Readout board 130 comprising 1 mm thickness was disposed below GEM layer 90 wherein GEM layer 90 was selected to comprise an elemental composition of approximate water-equivalency. Gas area 150 disposed above GEM layer 90 was disposed 100 cm from x-ray source XS, wherein x-ray source XS comprised a therapeutic linear accelerator from which a 6 MV X-ray spectrum was emitted.

Referring now more particularly to FIG. 1C, in an alternate configuration, grid screen 190 has been modeled as REXOLITE, wherein REXOLITE comprises a physical density of 1.05 g/cc with composition in weight percent of 9 for H, and 91 for C. It will be recognized by those skilled in the art that other materials could be substituted for REXOLITE without departing from the spirit of the present invention.

The dosimetric response of GEM-based dosimeter 40 is dictated by the dosimetric response of gas 70 in gaseous area 150. The dose applied to gas 70 was subsequently calculated at spatial resolutions characterized by the quantity of the elemental gas detector volumes. Spatial resolutions of 2 mm (horizontal direction or X)×4 cm (direction orthogonal to the horizontal direction or Y)×1 mm (direction of the beam or Z) and 2 mm×4 cm×2 mm were utilized. Calculations were performed for variations of X (the direction of off-axis distance in FIG. 2). The relatively large dimension of Y has little or no significant effect on the calculation of dose profile along X (4 cm in Y for the top three profiles in the legend box, FIG. 2). However, selection of the dimensions of X and Z facilitates proper investigation of dose response of the dosimeter 40 with high spatial resolution. This is because radiation traveling laterally within gaseous area 150 above GEM layer 90 is not absorbed as greatly in gas as it is in solid layers, and, thus, the radiation can generate crosstalk among neighboring elemental volumes, wherein as X and Z increase, the amount of crosstalk increases. Example I was not limited to the above two sizes of elemental volumes; other sizes were included by varying X and Z to investigate the crosstalk effect, and to determine the optimal size of elemental gas volumes.

For the configuration comprising REXOLITE screen 190, the dosimetric response of GEM-based dosimeter 40 is dictated by gas 70 contained in apertures 200 of screen 190. The dose applied to gas 70 was calculated at the spatial resolution characterized by the volume of gas 70 in apertures 200 and by pitch 210 between apertures 200. Aperture 200 diameter 220 as tested was approximately 3 mm; REXOLITE screen 190 thicknesses 250 were selectively approximately 2 and approximately 4 mm; pitch 210 was 4 mm, while web 230 between apertures 200 was 1 mm, and wherein web 230 comprised REXOLITE material. Web 230 functions to block crosstalk by absorbing laterally-scattered radiation. Diagonal distance 240 among apertures 200 was greater than lateral distance by a factor of 1.414. With grid screen 190 in place, diameter 220 of aperture 200, pitch 210 and thickness 250 define the spatial resolution of the GEM-based dosimeter 40.

In addition to Example I, all non-water components of dosimeter 40 were replaced with water to calculate the dose applied in a pure water medium (considered to be the gold standard of tissue-equivalency). Calculations were performed at the same geometrical distances as for gas layer 150 in Example I. The dose profile in $H_2O$ was found to be nearly invariable for slight changes of spatial resolutions at which profiles were acquired. Thus, the profile in $H_2O$ (2 mm×4 cm×2 mm) can be compared with the other four profiles obtained at different spatial resolutions.

From the results, FIG. 2 depicts two selected cases, wherein gas layer 150 above GEM layer 90 is filled with gas 70, and two selected cases, wherein a REXOLITE grid screen is further included. These results are compared with the above-referenced water standard. Good agreement with the water profile indicates ideal and optimal configuration. Good agreement was not observed for volumes of 2 mm×4 cm×2 mm or greater, particularly near beam penumbra region 260. Thus, the optimal dimension is 1 mm or less for Z, and 2 mm or less for X, wherein only gas 70 is present in gas layer 150. Therefore, the thickness 250 of gas layer 150 above GEM layer 90 should be less than 1 mm, unless the crosstalk effect is de-convolved from the acquired dose profile. The thickness of gas layer 150 equals thickness 250 of aperture/grid structure 190. For similar reasons, the sampling resolution in horizontal dimensions X and Y should be less than 2 mm.

For REXOLITE grid screen 190 contained within or replacing gas layer 150, the two profiles show close agreement with the water profile in FIG. 2, wherein the optimal dimension for grid screen 190 is 3 mm or less for the lateral dimensions of X and Y, with 1 mm spacing 230 and 4 mm or less in pitch 210 between apertures 200, and 2-4 mm for Z. Therefore, for REXOLITE grid screen 190, diameter 220 of apertures 200 should be less than approximately 3 mm, pitch 210 less than approximately 4 mm, and thickness 250 less than approximately 4 mm for measurements with relatively high spatial resolution. The profiles with REXOLITE show better agreement with the water profile than those for gas alone. This demonstrates that spaces 230 and 240, occupied by REXOLITE grid screen 190 among apertures 200 in screen 190, effectively absorb laterally-traveling radiation.

Figure 3:
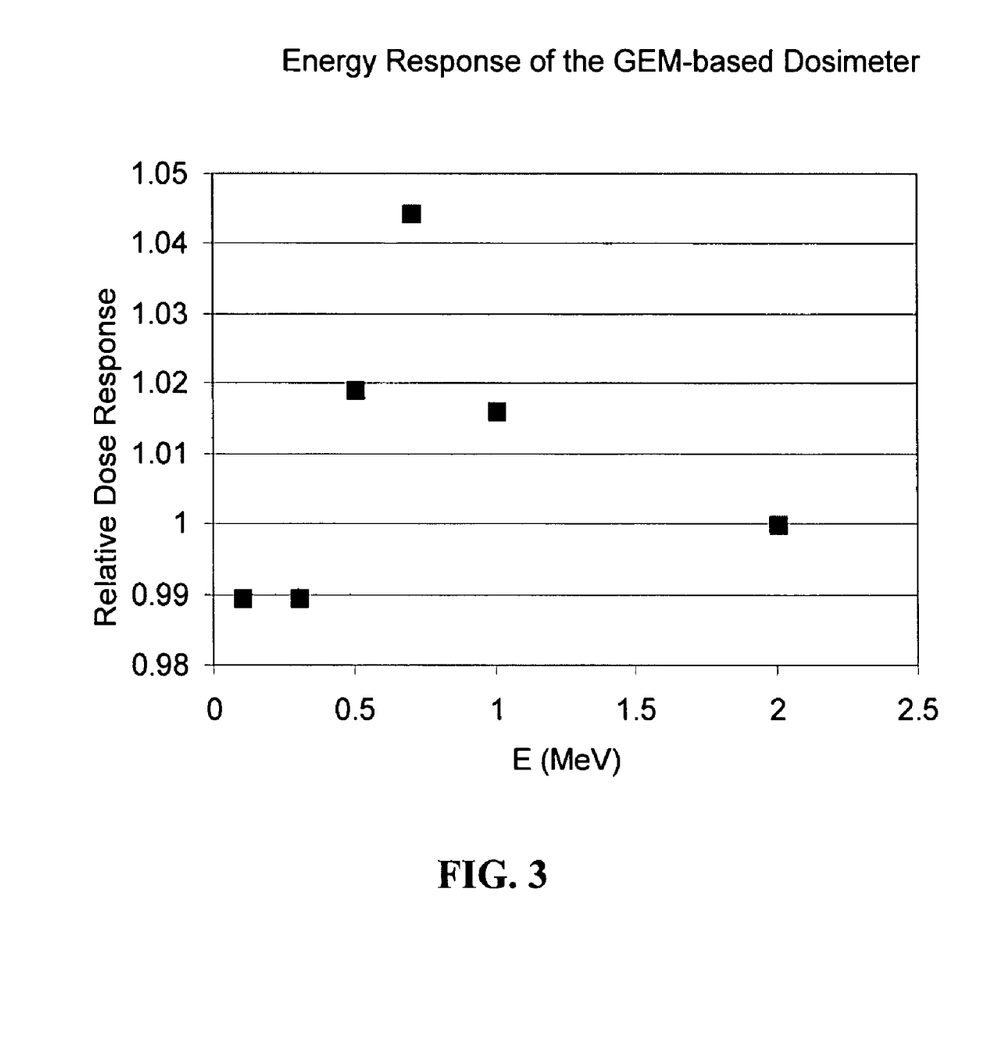

FIG. 3 depicts a computational result of energy dependence of TP gas 70 filling gas layer 150 above GEM layer 90. The same Monte Carlo calculations were utilized. For this simulation, the previous geometric constraints were applied, except that build-up phantom layer 20 comprised 5 mm thickness. An x-ray beam PB with a field size of 5 cm×5 cm, and comprising each of the energies depicted in FIG. 3, irradiated top surface 17 of build-up phantom layer 20. The dose applied to gas 70 was calculated for each selected energy level. The calculation voxel with-a size of 1 cm×1 cm×2 mm was centrally located to the incident beam axis. In order to calculate the dose for water, every non-water component of dosimeter 40 was replaced with water. The calculation was performed at the same geometrical location as for previous gas layer 150. Relative dose response, defined as the dose deposited in gas 70 divided by the dose deposited in water, was calculated for each selected energy level and normalized at 2 MeV. From 100 keV to 2 MeV, the relative energy dependence is within +4 and −1%. This is within the statistical error associated with the data in FIG. 3. This result indicates excellent energy-response characteristics for GEM-based dosimeter 40.

For most accurate and precise dose measurement, thickness 250 of gas area 150 above GEM layer 90 within the GEM-based dosimeter 40 should be less than 1 mm and the spatial resolution of gas layer 150, and therefore that of the GEM-based dosimeter 40 should be less than 2 mm in the horizontal dimension perpendicular to the beam entry direction.

The use of an aperture/grid structure formed from a tissue-equivalent non-conductive and radiation-resistant plastic material such as REXOLITE, prevents the crosstalk. In particular, while not limited to the following dimensions, an optimal configuration includes an aperture 200 diameter 220 of a few millimeters, an aperture 200 spacing 230 of a millimeter, and thickness 250 of a few to several millimeters. It will be recognized by those skilled in the art that other materials could be substituted for REXOLITE, other geometrical configurations could be alternatively utilized and still remain within the spirit of the present invention.

The foregoing description and drawings comprise illustrative embodiments of the present invention. Having thus described exemplary embodiments of the present invention, it should be noted by those skilled in the art that the within disclosures are exemplary only, and that various other alternatives, adaptations, and modifications may be made within the scope of the present invention. Merely listing or numbering the steps of a method in a certain order does not constitute any limitation on the order of the steps of that method. Many modifications and other embodiments of the invention will come to mind to one skilled in the art to which this invention pertains having the benefit of the teachings presented in the foregoing descriptions and the associated drawings. Although specific terms may be employed herein, they are used in a generic and descriptive sense only and not for purposes of limitation. Accordingly, the present invention is not limited to the specific embodiments illustrated herein, but is limited only by the following claims.

What is claimed is:

1. A dosimeter comprising:
 a gas electron multiplier and an alternative aperture/grid structure, wherein said gas electron multiplier is utilized as a detector.

2. The dosimeter of claim 1, further comprising a gas, wherein said gas is disposed within said dosimeter.

3. The dosimeter of claim 2, wherein said gas is disposed above a gas electron multiplier layer.

4. The dosimeter of claim 3, wherein said gas comprises a thickness, and wherein said thickness is less than 1 mm.

5. The dosimeter of claim 3, wherein said gas comprises a tissue-equivalent gas.

6. The dosimeter of claim 5, wherein said tissue-equivalent gas comprises TP gas.

7. The dosimeter of claim 5, wherein said tissue-equivalent gas comprises a mixture comprising a physical density of 0.001826 g/cc and a composition in weight percent of 10.27 for H, 56.89 for C, 29.34 for O, and 3.5 for N.

8. The dosimeter of claim 3, wherein said gas further comprises a layer, and wherein utilized spatial resolution of said gas layer in a horizontal dimension perpendicular to a beam entry direction is between 1 and 2 mm.

9. The dosimeter of claim 1, wherein said aperture/grid structure is disposed above a gas electron multiplier layer.

10. The dosimeter of claim 1, wherein apertures in said aperture/grid structure are filled with tissue-equivalent gas.

11. The dosimeter of claim 1, wherein said aperture/grid structure prevents crosstalk.

12. The dosimeter of claim 1, wherein said aperture/grid structure comprises polystyrene cross-linked with divinylbenzene.

13. The dosimeter of claim 1, wherein said aperture/grid structure comprises a thickness of approximately 2 to approximately 4 millimeters, a plurality of apertures having a diameter of approximately 3 millimeters, and a pitch between apertures of approximately 4 millimeters.

14. The dosimeter of claim 1, further comprising a tissue phantom.

15. The dosimeter of claim 1, further comprising at least one conductor/electrode, said at least one conductor/electrode comprising a cathode disposed above a gas layer and said gas electron multiplier.

16. The dosimeter of claim 15, wherein said at least one conductor/electrode is tissue equivalent.

17. The dosimeter of claim 1, further comprising a plurality of apertures, wherein said apertures have a diameter, and further comprising a pitch between apertures, wherein said diameter and said pitch define spatial resolution for signal registration.

18. The dosimeter of claim 1, further comprising at least one conductive electrode comprised of tissue-equivalent A-150 material.

19. The dosimeter of claim 1, wherein said alternative aperture/grid structure comprises tissue equivalent, nonconductive, insulating, radiation-resistant material.

20. A method of measurement of radiation doses, said method comprising the steps of:
    utilizing a dosimeter comprising a gas electron multiplier for dosimetry of therapeutic radiation and ionizing radiation, wherein said gas electron multiplier is utilized as a detector; and
    generating dosimetric signals utilizing energy absorption from ionizing radiation in a gas disposed above said gas electron multiplier and within apertures of an alternative aperture/grid structure disposed above said gas electron multiplier.

21. The method of claim 20, further comprising the step of:
    employing said gas electron multiplier, wherein said gas electron multiplier comprises fine spatial resolution for signal registration.

22. The method of claim 20, further comprising the step of:
    operating said dosimeter, wherein said dosimeter comprises said gas electron multiplier, and wherein said gas electron multiplier is operated in a mode selected from the group consisting of pulse mode and current mode.

23. The method of claim 20, further comprising the step of:
    operating said dosimeter, wherein said dosimeter comprises said gas electron multiplier, and wherein said gas electron multiplier is operated in an environment selected from the group consisting of gas-flow environments and gas-sealed environments.

24. The method of claim 20, further comprising the step of:
    preventing crosstalk of radiation utilizing said alternative aperture/grid structure.

25. The method of claim 20, further comprising the step of:
    utilizing tissue-equivalent A-150 conductive electrode material.

26. The method of claim 20, further comprising the steps of:
    utilizing a tissue-equivalent dosimeter wall, tissue-equivalent conductors/electrodes and insulators, said alternative aperture/grid structure, and a tissue-equivalent gas within a housing of said dosimeter.

27. A method of reading of radiation pattern and intensity, said method comprising the steps of:
    utilizing a gas electron multiplier-based dosimeter for reading therapeutic radiation position (multileaf collimator position) and intensity; and
    preventing crosstalk of radiation utilizing an alternative aperture/grid structure.

* * * * *